United States Patent [19]
Jackson

[11] Patent Number: 5,698,704
[45] Date of Patent: Dec. 16, 1997

[54] PROCESS FOR THE PREPARATION OF 4-OXOIMIDAZOLINIUM SALTS

[75] Inventor: Barry Jackson, Brig/Glis, Switzerland

[73] Assignee: Lonza AG, Gampel/Valais, Switzerland

[21] Appl. No.: 794,641

[22] Filed: Feb. 3, 1997

[30] Foreign Application Priority Data

Feb. 9, 1996 [CH] Switzerland ............... 00332/96

[51] Int. Cl.$^6$ .................. C07D 233/32; C07D 235/02
[52] U.S. Cl. .................. 548/300.7; 548/316.4; 548/325.5
[58] Field of Search ............... 548/300.7, 316.4, 548/325.5

[56] References Cited

U.S. PATENT DOCUMENTS 5,424,450 6/1995 Boswell et al. .

FOREIGN PATENT DOCUMENTS

WO91/14679 10/1991 WIPO .

*Primary Examiner*—Michael G. Ambrose
*Attorney, Agent, or Firm*—Fisher, Christen & Sabol

[57] ABSTRACT

4-Oxoimidazolinium salts of the general formula:

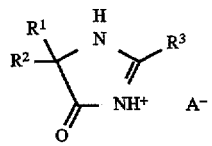

wherein $R^1$ and $R^2$ independently of one another are $C_{1-10}$-alkyl, $C_{2-10}$-alkenyl, $C_{3-7}$-cycloalkyl or optionally substituted aryl, arylalkyl, heteroaryl or heteroarylalkyl, or $R^1$ and $R^2$, together with the carbon atom to which they are bonded, form a three-membered to seven-membered saturated or unsaturated carbocyclic or heterocyclic ring, $R^3$ is a $C_{1-10}$-alkyl group, $C_{1-10}$-alkenyl group, $C_{3-7}$-cycloalkyl group, aryl group, arylalkyl group or heteroaryl group, and $A^-$ is an anion of a strong acid, are prepared by the cyclization of an α-acylaminonitrile in a nonaqueous solvent, in the presence of a lower alcohol and a strong acid. The compounds are intermediates for pharmaceutical active substances, for example, angiotensin II antagonists.

11 Claims, No Drawings

PROCESS FOR THE PREPARATION OF 4-OXOIMIDAZOLINIUM SALTS

BACKGROUND OF THE INVENTION

1. Field of The Invention

The invention relates to a process for the preparation of 4-oxoimidazolinium salts of the general formula:

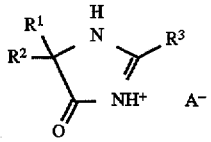     I wherein $R^1$ and $R^2$ independently of one another are $C_{1-10}$-alkyl, $C_{2-10}$-alkenyl, $C_{3-7}$-cycloalkyl or optionally substituted aryl, arylalkyl, heteroaryl or heteroarylalkyl, or $R^1$ and $R^2$, together with the carbon atom to which they are bonded, form a three-membered to seven-membered saturated or unsaturated carbocyclic or heterocyclic ring, $R^3$ is a $C_{1-10}$-alkyl group, a $C_{2-10}$-alkenyl group, a $C_{3-7}$-cycloalkyl group or an optionally substituted aryl group, arylalkyl group or heteroaryl group, and $A^-$ is an anion of a strong acid.

2. Background Art

Compounds of the type of the 4-oxoimidazolinium salts of general formula I, or the 2-imidazolin-4-ones [1H-imidazol-5(4H)-ones] on which these salts are based, are important intermediates in the synthesis of pharmaceutical active substances, for example, angiotensin II antagonists (WO-A 91/14679, U.S. Pat. No. 5,424,450). They have hitherto been prepared, for example, by the acylation of α-aminonitriles to the corresponding amidonitriles (=α-acylaminonitriles, also known as "aliphatic Reissert compounds"), acid hydrolysis of the nitrile group to the carbamoyl group and subsequent base-catalyzed cyclization of the resultant amidoamide (U.S. Pat. No. 5,424,450, Scheme 3). The order of the acylation and the hydrolysis can also be reversed (WO-A 91/14679, pp. 25 and 26). One disadvantage of these processes is the need to change between acid and basic reaction conditions, which requires neutralization each time and leads to the formation of correspondingly large amounts of waste salts.

BROAD DESCRIPTION OF THE INVENTION

The object of the invention is to provide a simpler process for the 4-oxoimidazolinium salts of general formula I which produces less waste. Other objects and advantages of the invention are set out herein or are obvious herefrom to one skilled in the art.

The objects and advantages of the invention are achieved by the process of the invention.

The invention involves a process for the preparation of 4-oxoimidazolinium salts of the general formula:

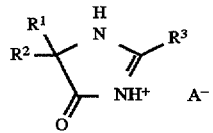     I wherein $R^1$ and $R^2$ independently of one another are $C_{1-10}$-alkyl, $C_{2-10}$-alkenyl, $C_{3-7}$-cycloalkyl or optionally substituted aryl, arylalkyl, heteroaryl or heteroarylalkyl, or $R^1$ and $R^2$, together with the carbon atom to which they are bonded, form a three-membered to seven-membered saturated or unsaturated carbocyclic or heterocyclic ring, $R^3$ is a $C_{1-10}$-alkyl group, a $C_{2-10}$-alkenyl group, a $C_{3-7}$-cycloalkyl group or an optionally substituted aryl group, arylalkyl group or heteroaryl group, and $A^-$ is an anion of a strong acid, comprising cyclizing an α-acylaminonitrile of the general formula:

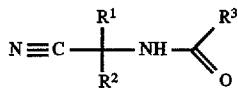     II wherein $R^1$, $R^2$ and $R^3$ are as defined above, in a nonaqueous solvent, in the presence of a lower alcohol and a strong acid of the general formula HA, wherein A is as defined above (that is, A is the chemical moiety of anion $A^-$).

$C_{1-10}$-alkyl groups are to be understood, above and below, as meaning both linear and branched primary, secondary and tertiary alkyl groups having 1 to 10 carbon atoms. Correspondingly, $C_{2-10}$-alkenyl groups are to be understood as meaning both linear and branched primary, secondary and tertiary hydrocarbon radicals having one or more double bonds in any position. Aryl groups are to be understood as meaning monocyclic or polycyclic aromatic groups, especially phenyl and naphthyl. Arylalkyl groups are to be understood as meaning lower alkyl groups substituted by aryl groups, especially benzyl and phenylethyl. Heteroaryl groups are to be understood as meaning especially groups such as furyl or thienyl (thiophenyl) and, correspondingly, heteroarylalkyl is to be understood as meaning groups such as furfuryl (furylmethyl) or thenyl (thiophenylmethyl). The aryl, arylalkyl, heteroaryl or heteroarylalkyl groups can optionally carry one or more substituents, for example, $C_{1-4}$-alkyl, $C_{1-4}$-alkoxy or halo.

Preferably an acid which is hydrogen halides, sulfuric acid, formic acid, methanesulfonic acid or trifluoroacetic acid, is used as the strong acid HA. Most preferably hydrochloric acid is used as the strong acid HA. Preferably a solvent which is an aromatic hydrocarbon or a halogenated hydrocarbon is used as the nonaqueous solvent. Preferably methanol, ethanol, propanol, butanol or isopropyl alcohol is used as the lower alcohol and the nonaqueous solvent. Preferably the compound used as the α-acylaminonitrile (II) is one in which $R^1$ and $R^2$, together with the carbon atom to which they are bonded, form a cyclopentane or a cyclohexane ring. Preferably the compound used as the α-acylaminonitrile (II) is one in which $R^3$ is a $C_{1-6}$-alkyl group.

DETAILED DESCRIPTION OF THE INVENTION

It has been found that, surprisingly, the 4-oxoimidazolinium salts (I) can be obtained directly from α-acylaminonitriles of the general formula:

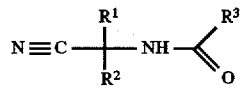     II wherein $R^1$, $R^2$ and $R^3$ are as defined above, in a nonaqueous solvent, in the presence of a lower alcohol and a strong acid of the general formula HA, wherein A or the anion $A^-$ is as defined above, in one step, without the isolation of an intermediate and without a neutralization step.

The α-acylaminonitriles (II) can be prepared by known methods, for example, by means of a Strecker reaction of the corresponding carbonyl compounds $R^1$—C(=O)—$R^2$ with hydrocyanic acid and ammonia and subsequent acylation of the resulting α-aminonitrile with a carboxylic acid chloride $R^3$COCl.

Both inorganic acids ("mineral acids") and organic acids, for example, sulfonic acids, are suitable as the strong acid HA. It is preferable to use an acid from the group consisting of the hydrogen halides, sulfuric acid, formic acid, trifluoroacetic acid and methanesulfonic acid. Hydrochloric acid is particularly preferred. The acid is preferably used is an amount of 1 to 2 equivalents, more preferably of 1.1 to 1.5 equivalents, per mole of starting material.

As the nonaqueous solvent it is preferable to use a solvent from the group comprising the aromatic hydrocarbons, such as, benzene, toluene or xylene, or from the group comprising the halogenated hydrocarbons, for example, dichloromethane.

A particularly preferred embodiment is one in which the lower alcohol is used simultaneously as the nonaqueous solvent. Methanol, ethanol, propanol, butanol and isopropyl alcohol are particularly suitable for this purpose.

The process according to the invention is preferably used for the preparation of 4-oxoimidazolinium salts (I) which are spiro compounds wherein $R^1$ and $R^2$, together with the carbon atom to which they are bonded, form a cyclopentane or cyclohexane ring. It is also preferable to prepare 4-oxoimidazolinium salts (I) in which $R^3$ is a $C_{1-6}$-alkyl group.

The reaction temperature is advantageously 0° to 120° C., preferably 20° to 100° C.

Of course, it is also within the framework of the invention to convert the 4-oxoimidazolinium salts (I) to the corresponding imidazolin-4-ones with bases.

The following Examples illustrate how the process according to the invention is carried out, without thereby implying any limitation.

EXAMPLE 1

2-Butyl-1,3-diazaspiro[4.4]non-2-en-4-one monohydrochloride

[I, $R^1+R^2$=—$(CH_2)_4$—, $R^3$=n-butyl]

9.39 g (39 mmol) of a freshly prepared solution of hydrogen chloride in ethanol (15.15 percent by weight) was added to 6.80 g (30 mmol) of N-(1-cyanocyclopentyl)-pentanamide (prepared from cyclopentanone by means of a Strecker synthesis to give 1-aminocyclopentanecarbonitrile and acylation with pentanoyl chloride, content 85.7 percent) in 28 g of anhydrous ethanol. The mixture was heated to 50° C. under nitrogen and stirred at this temperature for 3.1 hours. It was then cooled to 1° C. and left to stand at this temperature for 1 hour. The product which had precipitated out was filtered off, washed with 10 ml of ice-cold ethanol and dried at 40° C./24 mbar. The yield of the product was 4.05 g (58 percent) of colorless crystals, content 98.3 percent (HPLC).

EXAMPLE 2

2-Butyl-1,3-diazaspiro[4.4]non-2-en-4-one monohydrochloride

[, $R^1+R^2$=—$(CH_2)_4$—, $R^3$=n-butyl]

A solution of 6.88 g (30 mmol) of N-(1-cyanocyclopentyl)pentanamide (content 84.7 percent) was added dropwise over 15 minutes at 70° C., under nitrogen, to a mixture of 9.84 g (45 mmol) of a 16.7 percent solution of hydrogen chloride in propanol and 11.71 g of dried propanol, and a solid precipitated out. The mixture was stirred for a further 1.7 hours at 70° C., cooled to 1° C. and left to stand for 1 hour at this temperature. The product was then filtered off, washed with 10 ml of ice-cold propanol and dried at 40° C./24 mbar. The yield of the product was 5.74 g (79 percent), content 95.4 percent (titrimetry). Other data concerning the product was:

IR (KBr): ν=1779; 1642; 1517 cm$^{-1}$
$^1$H NMR (DMSO-d$_6$): δ=13.64 (s, 2H); 2.80 (m, 2H); 1.7–2.0 (m, 10H); 1.34 (m, 2H); 0.91 (t, J=7.3 Hz, 3H).
$^{15}$N NMR(DMSO-d$_6$): δ=−211.8; −219.6 (standard: acetanilide).

EXAMPLE 3

2-Butyl-1,3-diazaspiro[4.4]non-2-en-4-one monohydrochloride [I, $R^1+R^2$=—$(CH_2)_4$—, $R^3$=n-butyl]

6.88 g (30 mmol) of N-(1-cyanocyclopentyl)pentanamide (content 84.7 percent) was stirred for 44 hours at room temperature, under nitrogen, with 27.3 g of dried isopropyl alcohol and 9.92 g (39 mmol) of a freshly-prepared 14.33 percent solution of hydrogen chloride in isopropyl alcohol. The mixture was then cooled to 1° C. and left to stand for ½hour at this temperature. The product which had precipitated out was filtered off, washed with 10 ml of ice-cold isopropyl alcohol and dried at 40° C./24 mbar. The yield of the product was 3.04 g (44 percent), content 99.7 percent (HPLC).

EXAMPLE 4

2-Butyl-1,3-diazaspiro[4.4]non-2-en-4-one monohydrochloride
[I, $R^1+R^2$=—$(CH_2)_4$—, $R^3$ =n-butyl]

6.88 g (30 mmol) of N-(1-cyanocyclopentyl)pentanamide (content 84.7 percent), 16.66 g of dried butanol and 10.06 g (39 mmol) of a freshly-prepared 14.13 percent solution of hydrogen chloride in butanol were heated to the reflux point (preheated oil bath) under nitrogen, with stirring, and product precipitated out as soon as the internal temperature reached ca. 100° C. After 2.9 hours of reflux (115° C.), the mixture was cooled to 1° C. and left to stand for 1 hour at this temperature. The product which had precipitated out was filtered off, washed with 10 ml of ice-cold butanol and dried at 40° C./24 mbar. The yield of the product was 4.93 g (66 percent), content 92.7 percent (HPLC).

EXAMPLE 5

2-Amino-2-methylbutanenitrile 40.0 g (800 mmol) of sodium cyanide was dissolved in 78 ml of water. A solution of 47.5 g (880 mmol) of ammonium chloride in a mixture of 70 ml of concentrated aqueous ammonia solution (0.92 mol of NH$_3$) and 118 ml of water was added to the sodium cyanide solution at room temperature under nitrogen. A mixture of 51.8 g (714 mmol) of butanone and 76 ml of methanol (dried over a molecular sieve) was then added dropwise at 20° to 25° C. (water bath). The reaction mixture was stirred for ca. 2 hours at room temperature and then heated to 60° C. and kept at this temperature for ca. 1 hour. After cooling, the reaction mixture was extracted once with 200 ml and then twice with 100 ml of dichloromethane. The combined organic phases was dried over 20 g of sodium sulfate, filtered and diluted to 700 g of solution with dichloromethane. The resultant solution was used for the acylation without further working-up. The yield of the product was 94 percent (GC).

EXAMPLE 6

N-(1-Cyano-1-methylpropyl)pentanamide
[II, $R^1$=Et, $R^2$=Me, $R^3$=n-butyl]

39.6 (389 mmol) of triethylamine was added at room temperature, under nitrogen, to 350 g of a solution of 2-amino-2-methylbutanenitrile in dichloromethane (from Example 5, max. 357 mmol). 47.9 g (389 mmol) of pentanoyl chloride was then added dropwise over 1 hour at 10° to 25° C. (cooling) and a solid (triethylammonium chloride) precipitated out. When the addition had ended, the reaction mixture was stirred for a further 2 hours at room temperature. 100 ml of water was then added and the phases were separated. The organic phase was washed with 100 ml of 1 N hydrochloric acid and then with 100 ml of water, dried over 20 g of sodium sulfate and finally concentrated under a water-jet vacuum. The yield of the product was 50.2 g of oil, content (GC) 86 percent (corresponds to 66 percent of theory). Other data concerning the product was:

IR (film): $\nu$=3305; 2230; 1656; 1535 cm$^{-1}$.

$^1$H NMR (DMSO-d$_6$): $\delta$=8.13 (s, 1H); 2.14 (t, J=7.3 Hz, 2H); 1.8 (m, 2H); 1.52 (s, 3H); 1.4–1.5 (m, 2H); 1.29 (m, 2H); 0.98 (t, J=7.3 Hz, 3H); 0.88 (t, J =7.2 Hz, 3H).

EXAMPLE 7

2-Butyl-4-ethyl-4-methyl-1H-imidazol-5(4H)-one hydrochloride [I, R$^1$=Et, R$^2$=Me, R$^3$=n-butyl, A$^-$=Cl$^-$]

19.05 g (90 mmol) of the N-(1-cyano-1-methylpropyl) pentanamide from Example 6 was stirred at 30° C. for 6½ hours in a mixture of 25.6 g of a 16.7 percent solution of hydrogen chloride in propanol (117 mmol of HCl) and 53.8 g of propanol (dried over a molecular sieve) under nitrogen. The resultant clear yellow solution was then placed in the refrigerator overnight. The crystals which had precipitated out were filtered off, washed with 10 ml of ice-cold propanol and dried at 40° C./24 mbar. The yield of the product was 5.38 g (27 percent) of white crystals, content (HPLC) 99.5 percent. Other data concerning the product was:

IR (KBr): $\nu$=1779; 1638; 1519 cm$^{-1}$.

$^1$H NMR (DMSO-d$_6$): $\delta$=13.71 (s, 1H); 2.87 (m, 2H); 1.7–1.8 (m, 4H); 1.43 (s, 3H); 1.37 (m, 2H); 0.92 (t, J=7.4 Hz, 3H); 0.83 (t, J=7.3 Hz, 3H).

$^{15}$N NMR (DMSO-d$_6$): $\delta$=−215.4; −217.7.

EXAMPLE 8

2-Amino-2-phenylpropanenitrile 40.0 g (800 mmol) of sodium cyanide and 47.5 g (880 mmol) of ammonium chloride were suspended in 196 ml of methanol under nitrogen. A mixture of 87.5 g (714 mmol) of acetophenone and 76 ml of methanol (dried over a molecular sieve) was then added dropwise over 15 minutes at room temperature. The reaction mixture was stirred for a further 1 hour at room temperature and then heated to 40° C., kept at this temperature for 5½ hours and stirred for a further 2 days at 22° C. The resultant orange suspension was filtered through a glass frit and the flitrate was concentrated to ¼ of the volume under vacuum at max. 35° C. and filtered again. This flitrate (ca. 100 g) was diluted to 400 g with diethyl ether and filtered once more. 11.4 g (1.1 equivalents) of hydrogen chloride was then introduced into the resultant clear orange-red solution over 70 minutes and a light-colored solid precipitated out. The mixture was left to stand in the refrigerator overnight and the supernatant was then decanted from the precipitate. The precipitate was washed with 50 ml of diethyl ether and dissolved in 100 ml of water. The aqueous solution (pH ≈2.5) was adjusted to pH 8.7 with concentrated sodium hydroxide solution and then extracted with 3×100 ml of diethyl ether. The combined ether extract was dried over 20 g of sodium sulfate and then evaporated under vacuum. The residue was suspended with twice 15 ml of 15 toluene and concentrated to dryness under vacuum again. The yield of the product was 56.2 g, content ($^1$H NMR) 83 percent (corresponds to 45 percent of theory, based on acetophenone). Other data concerning the product was:

IR (NaCl): $\nu$=3378; 3313; 2224 cm$^{-1}$.

$^1$H NMR (CDCl$_3$): $\delta$=7.63–7.68 (m, 2H); 7.30–7.43 (m, 3H); 2.08 (s, 2H);1.74 (s, 3H).

EXAMPLE 9

N-(1-Cyano-1-phenylethyl)pentanamide [I, R$^1$=Ph, R$^2$=Me, R$^3$=n-butyl]

46.1 g (375 mmol) of pentanoyl chloride was added dropwise over 55 minutes at 12° to 23° C. (cooling), under nitrogen, to 55.8 g of 2-amino-2-phenylpropanenitrile (from Example 8, ca. 0.34 mol) and 38.1 g (375 mmol) of triethylamine in 280 g of dichloromethane, and a solid (triethylammonium chloride) precipitated out. When the addition had ended, the reaction mixture was stirred for a further 2 hours at room temperature. 100 ml of water was then added and the phases were separated. The organic phase was washed with 100 ml of 1 N hydrochloric acid and then with 100 ml of water, dried over 20 g of sodium sulfate and finally concentrated at 50° C. under a water-jet vacuum. For purification 40.0 g of the residue (total amount of beige solid 84.1 g) was recrystallized from 230 ml of boiling ethyl acetate/cyclohexane (70:30), cooled to room temperature, filtered off on a glass frit, washed with 50 ml of cyclohexane and dried at 40° C./30 mbar. The yield of the product was 31.71 of white crystals (extrapolated to the total amount of crude product: 66.7 g, corresponds to 84 percent of theory, based on the aminonitrile). Other data concerning the product was:

IR (KBr): $\nu$=2228; 1657; 1539 cm$^{-1}$.

$^1$H NMR (DMSO-d$_6$): $\delta$=7.3–7.4 (m, 5H); 7.03 (s, 1H); 2.15 (t, J=7.6 Hz, 2H); 1.77 (s, 3H); 1.55 (m, 2H); 1.30 (m, 2H); 0.89 (t, J=7.3 Hz, 3H).

EXAMPLE 10

2-Butyl-4-methyl-4-phenyl-1H-imidazol-5(4H)-one hydrochloride [I, R$^1$=Ph, R$^2$=Me, R$^3$=n-butyl, A$^-$=Cl$^{13}$)

8.49 g (30 mmol) of the N-(1-cyano-1-phenylethyl) pentanamide from Example 9 was heated to 50° C. in a mixture of 9.2 g of a 15.5 percent solution of hydrogen chloride in propanol (30 mmol of HCl) and 33.3 g of propanol (dried over a molecular sieve), under nitrogen, and stirred at this temperature for 3¼ hours. The resultant clear yellow solution was then left to stand overnight at room temperature and subsequently evaporated to dryness at 50° C./16 mbar. The residue (17.76 g) was suspended in 30 ml of acetone for 1¼ hours at room temperature. The suspension was filtered through a glass frit and the filter cake was washed with 10 ml of acetone and dried at 40° C./24 mbar. The yield of the product was 5.47 of a white solid, content (titrimetry) 98 percent (corresponds to 67 percent of theory, based on the aminonitrile). Other data concerning the product was:

IR (KBr): $\nu$=1787; 1633; 1517 cm$^{-1}$.

$^1$H NMR (DMSO-d$_6$): $\delta$=14.0 (s, 2H); 7.3–7.6 (m, 5H); 2.99 (t, J=7.5 Hz, 2H); 1.7–2.0 (m, 2H); 1.85 (s, 3H); 1.38 (m, 2H); 0.93 (t, J=7.5 Hz, 3H).

$^{15}$N NMR (DMSO-d$_6$): $\delta$=−213.5; −220.0.

What is claimed is:

1. A process for the preparation of a 4-oxoimidazolinium salt of the formula:

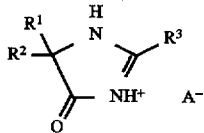

wherein $R^1$ and $R^2$ independently of one another are $C_{1-10}$-alkyl, $C_{2-10}$-alkenyl, $C_{3-7}$-cycloalkyl or optionally substituted aryl, arylalkyl, heteroaryl or heteroarylalkyl, or $R^1$ and $R^2$, together with the carbon atom to which they are bonded, form a three-membered to seven-membered saturated or unsaturated carbocyclic or heterocyclic ring, $R^3$ is a $C_{1-10}$-alkyl group, a $C_{2-10}$-alkenyl group, a $C_{3-7}$-cycloalkyl group or an optionally substituted aryl group, arylalkyl group or heteroaryl group, and $A^-$ is an anion of a strong acid, comprising cyclizing an α-acylaminonitrile of the formula:

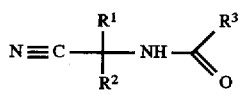

wherein $R^1$, $R^2$ and $R^3$ are as defined above, in a nonaqueous solvent, in the presence of a lower alcohol and a strong acid of the general formula HA, wherein A is as defined above.

2. The process according to claim 1 wherein an acid selected from the group consisting of the hydrogen halides, sulfuric acid, formic acid, methanesulfonic acid and trifluoroacetic acid, is used as the strong acid HA.

3. The process according to claim 2 wherein hydrochloric acid is used as the strong acid HA.

4. The process according to claim 2 wherein a solvent selected from the group consisting of the aromatic hydrocarbons and the halogenated hydrocarbons, is used as the nonaqueous solvent.

5. The process according to claim 2 wherein methanol, ethanol, propanol, butanol or isopropyl alcohol is used as the lower alcohol and the nonaqueous solvent.

6. The process according to claim 5 wherein the compound used as the α-acylaminonitrile (II) is one in which $R^1$ and $R^2$, together with the carbon atom to which they are bonded, form a cyclopentane or cyclohexane ring.

7. The process according to claim 6 wherein the compound used as the α-acylaminonitrile (II) is one in which $R^3$ is a $C_{1-6}$-alkyl group.

8. The process according to claim 1 wherein a solvent selected from the group consisting of the aromatic hydrocarbons and the halogenated hydrocarbons, is used as the nonaqueous solvent.

9. The process according to claim 1 wherein methanol, ethanol, propanol, butanol or isopropyl alcohol is used as the lower alcohol and the nonaqueous solvent.

10. The process according to claim 1 wherein the compound used as the α-acylaminonitrile (II) is one in which $R^1$ and $R^2$, together with the carbon atom to which they are bonded, form a cyclopentane or cyclohexane ring.

11. The process according to claim 1 wherein the compound used as the α-acylaminonitrile (II) is one in which $R^3$ is a $C_{1-6}$-alkyl group.

* * * * *